(12) United States Patent
Fergason

(10) Patent No.: US 7,161,135 B2
(45) Date of Patent: Jan. 9, 2007

(54) MULTI-STAGE SENSOR FOR AN AUTO-DARKENING LENS FOR USE IN WELDING AND METHOD

(75) Inventor: John D. Fergason, Cupertino, CA (US)

(73) Assignee: Lightswitch Safety Systems, Inc., Mountain View, CA (US)

(\*) Notice: Subject to any disclaimer, the term of this patent is extended or adjusted under 35 U.S.C. 154(b) by 119 days.

(21) Appl. No.: 10/884,049

(22) Filed: Jul. 2, 2004

(65) Prior Publication Data

US 2005/0001155 A1 Jan. 6, 2005

Related U.S. Application Data

(60) Provisional application No. 60/484,703, filed on Jul. 3, 2003.

(51) Int. Cl.
  *G01J 1/10* (2006.01)
  *G01J 1/44* (2006.01)
  *A61F 9/06* (2006.01)
  *F16P 1/06* (2006.01)

(52) U.S. Cl. .............. 250/221; 250/201.1; 250/214 B; 2/7; 2/15; 219/147

(58) Field of Classification Search .............. 250/221, 250/214 B, 201.1; 2/7, 15; 219/147; 359/229, 359/601; 349/13, 14
See application file for complete search history.

(56) References Cited

U.S. PATENT DOCUMENTS

| | | |
|---|---|---|
| 3,731,986 A | 5/1973 | Fergason |
| 3,881,809 A | 5/1975 | Fergason et al. |
| 4,039,254 A | 8/1977 | Harsch |
| RE29,684 E | 6/1978 | Gordon |
| 4,385,806 A | 5/1983 | Fergason |
| 4,436,376 A | 3/1984 | Fergason |
| 4,540,243 A | 9/1985 | Fergason |
| 4,582,396 A | 4/1986 | Bos et al. |

(Continued)

FOREIGN PATENT DOCUMENTS

CA 2076777 2/1993

(Continued)

OTHER PUBLICATIONS

International Search Report relating to application PCT/US2004/021335, dated mailed Dec. 17, 2004.

*Primary Examiner*—Stephone B. Allen
*Assistant Examiner*—Davienne Monbleau
(74) *Attorney, Agent, or Firm*—Renner, Otto, Boisselle & Sklar, LLP

(57) ABSTRACT

A multi-stage control for an auto-darkening lens includes a first detector to detect initiation of welding and a second detector to detect continuation of welding after welding has been initiated. The first detector has relatively low sensitivity and fast response time; and the second detector has relatively high sensitivity that can be altered as may be necessary, relatively slow response time to allow opportunity to determine whether welding is continuing as inputs indicative of welding, and adaptive filtering to filter ambient effects and the like from such inputs to avoid false detection of welding. A method of enhancing operation of an auto-darkening lens control that has a detector and associated circuitry to detect initiation of welding substantially independently of time based filtering and to maintain detecting of welding using time based discrimination, comprising coupling control signals and power to an auto-darkening lens via a substantially unimpeded path from a detector to the auto-darkening lens.

36 Claims, 4 Drawing Sheets

U.S. PATENT DOCUMENTS

| | | |
|---|---|---|
| RE32,521 E | 10/1987 | Fergason |
| 5,074,647 A | 12/1991 | Fergason et al. |
| 5,208,688 A | 5/1993 | Fergason et al. |
| 5,248,880 A | 9/1993 | Fergason |
| 5,252,817 A | 10/1993 | Fergason et al. |
| 5,347,383 A | 9/1994 | Fergason |
| 5,510,609 A | 4/1996 | Ackermann |
| 5,519,122 A | 5/1996 | Ajito et al. |
| 5,519,522 A | 5/1996 | Fergason |
| 5,959,705 A | 9/1999 | Fergason |
| 6,067,129 A | 5/2000 | Fergason |
| 6,070,264 A | 6/2000 | Hamilton |
| 6,242,711 B1 | 6/2001 | Cooper |
| 6,369,952 B1 | 4/2002 | Rallison et al. |

FOREIGN PATENT DOCUMENTS

| | | |
|---|---|---|
| DE | 41 28 291 A1 | 3/1993 |
| EP | 1 118 899 A1 | 7/2001 |

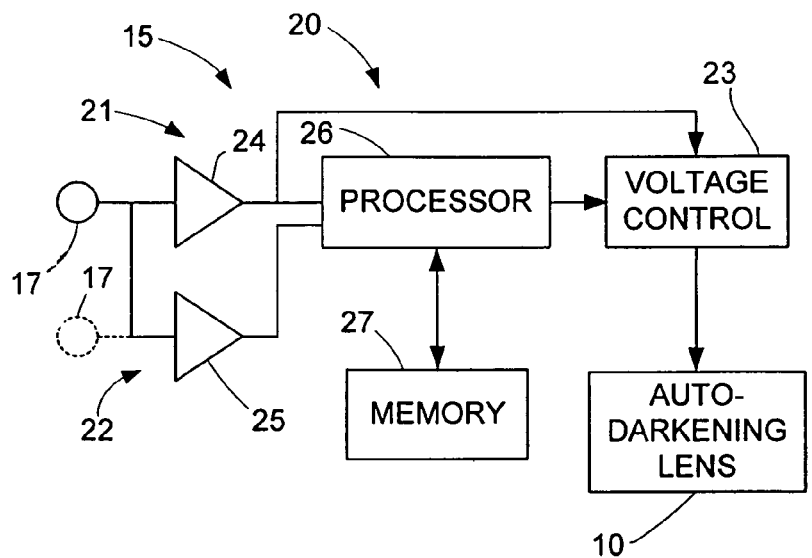
FIG. 3
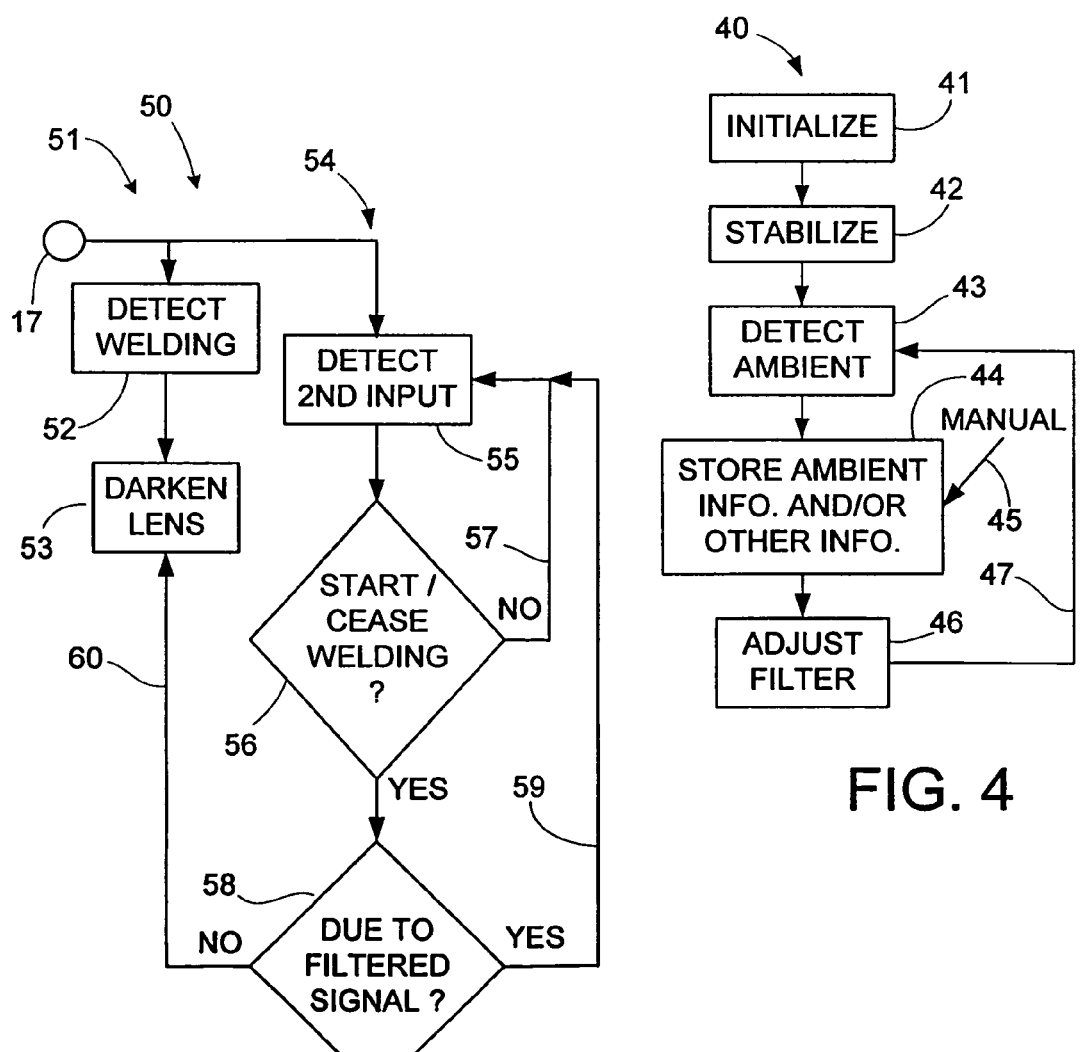
FIG. 4
FIG. 5

MULTI-STAGE SENSOR FOR AN AUTO-DARKENING LENS FOR USE IN WELDING AND METHOD

CROSS-REFERENCE TO RELATED APPLICATION

This application claims the benefit of U.S. Provisional Application Ser. No. 60/484,703, filed Jul. 3, 2003.

TECHNICAL FIELD

The present invention relates generally, as indicated, to a multi-stage sensor for an auto-darkening lens and method, and more particularly, to a multi-stage sensor to operate an auto-darkening welding lens promptly to cause dark state and to maintain dark state during continuation of welding.

BACKGROUND

As is described further in the background discussion below, photosensor devices associated with auto-darkening lenses have been used in the past to detect welding. For example, a photosensor and an associated circuit (sometimes referred to as "control circuit," "operating circuit," "drive circuit," etc.) respond to the bright light at the beginning of welding, e.g., when a person ignites a welding torch, e.g., flame type, electric arc type, etc., to carry out a welding process. Upon detecting the bright light that occurs at the start of welding, the photosensor and associated circuit cause the shutter of an auto-darkening welding lens to go automatically to a dark state, whereby light transmission through the welding lens is reduced and the eyes of the person carrying out the welding process are protected from the bright light. When the bright light ceases, which would indicate cessation of welding, the photosensor and associated circuit cause the auto-darkening lens to increase light transmission to a relatively clear or bright state.

Reference herein to light may be visible light, ultraviolet light, infrared light, or other types of electromagnetic energy that would affect the eyes of a person, such that the electromagnetic energy can be attenuated by the use of an auto darkening lens. The description below is presented with respect to use of the invention in connection with attenuating light resulting from a welding process (sometimes referred to as "welding"), but it will be appreciated that features of the invention may be used in other environments and in connection with industrial processes other than welding, etc. Also, it will be appreciated that although a photosensor is described as the device for detecting bright light occurring during welding, other types of sensors may be used.

The intensity of light produced during welding may vary. For example, at the start of welding, the light may be very bright, but as welding continues, the light intensity may diminish. Also, the light intensity may fluctuate during sputtering, or may fluctuate in relation to the electrical energy, e.g., the AC sine wave characteristic, that may be employed in electric arc welding. Ambient light also may affect the sensor and cause welding incorrectly to be detected.

Normally the sensor or sensors for an automatic darkening lens (auto-darkening lens) and the associated circuitry are set to a given sensitivity, and any signal that is detected that exceeds a threshold level at which such sensitivity is set, whether the signal is an AC signal or a DC signal, will cause the circuitry to operate the auto-darkening lens to a dark state. A conventional approach to maintain the auto-darkening lens in dark state even after the initial striking of an arc, e.g., after which the light intensity may decrease, has been to reduce the threshold level or to increase the sensitivity of the sensor and/or associated circuit so that it continues to maintain the auto-darkening lens in the dark state even under the diminished incident light. However, such increased sensitivity or reduced threshold can cause the auto-darkening lens to remain in the dark state even when welding is not occurring, such as, for example, due to ambient light conditions. The present invention as described further below addresses this issue.

In the description herein reference will be made to a lens (also sometimes referred to as "welding lens," "welding filter," "shutter," and the like), and to an automatically darkening lens (sometimes referred to as auto-darkening lens) that is able to operate automatically to control transmission of light. The lens may be a light shutter type of a device that is able to control light transmission without distorting, or at least with relatively minimal distortion, of the light and the image characteristics carried by the light or represented by the light. Therefore, when a person looks through the lens, the image seen would be substantially the same as the image seen without the lens, except that the intensity of the light transmitted through the lens may be altered depending on the operative state of the lens. The lens may be used in a welding helmet, and the lens may be used in other types of devices, such as goggles, spectacles, face masks, e.g., for industry (such as in an industrial plant or to protect outdoor or indoor electrical workers), for dentistry to protect the face of a dentist in the operative, respirator systems, nuclear flash eye protection devices, and other types of helmets, etc. Such devices usually are employed to protect the face or the eyes of a person, as is known, for example, in the field of welding and in other fields, too. Further, the lenses may be used in various other places to protect workers from bright light that could present a risk of injury.

For the purposes of providing eye protection, usually a welding lens provides light blocking characteristics in the visible, Infrared and ultraviolet wavelength ranges. The actual ranges may be determined by the components of the lens, the arrangement of those components, and so forth. One example of such a welding lens is U.S. Pat. No. 5,519,522. The lens assembly disclosed In that patent includes several liquid crystal cell light shutters, several plane polarizers, and a reflector or band pass filter, which is able to reflect ultraviolet and infrared electromagnetic energy and possibly also some electromagnetic energy in the visible wavelength range. The several liquid crystal cells, for example, may be birefringent liquid crystal cells sometimes referred to as surface mode liquid crystal cells or pi-cells.

Examples of liquid crystal cells, lenses using them and drive circuits are described in U.S. Pat. Nos. 5,208,688, 5,252,817, 5,248,880, 5,347,383, and 5,074,647. In U.S. Pat. No. 5,074,647, several different types of variable polarizer liquid crystal devices are disclosed. Twisted nematic liquid crystal cells used in an automatic shutter for welding helmets are disclosed in U.S. Pat. Nos. 4,039,254 and Re. 29,684. Exemplary birefringent liquid crystal cells useful as light shutters in the present invention are disclosed in U.S. Pat. Nos. 4,385,806, 4,436,376, 4,540,243, 4,582,396, and Re. 32,521 and exemplary twisted nematic liquid crystal cells and displays are disclosed in U.S. Pat. Nos. 3,731,986 and 3,881,809. Another type of liquid crystal light control device is known as a dyed liquid crystal cell. Such a dyed cell usually includes nematic liquid crystal material and a pleochroic dye that absorbs or transmits light according to orientation of the dye molecules. As the dye molecules tend to assume an alignment that is relative to the alignment of the liquid crystal structure or directors, a solution of liquid crystal material and dye placed between a pair of plates will absorb or transmit light depending on the alignment of the liquid crystal material. Thus, the absorptive characteristics of the liquid crystal device can be controlled as a function of applied electric field.

As is disclosed in several of the above patents, the respective shutters may have one or more operational characteristics (sometimes referred to as modes or states). One example of such an operational characteristic is the shade number; this is the darkness level or value of the shutter when it is in the light blocking mode. Another exemplary operational characteristic is the delay time during which the shutter remains in a dark state after a condition calling for the dark state, such as detection of the bright light occurring during welding, has ceased or detection thereof has terminated or been interrupted. Still another operational characteristic is sensitivity of the detection circuit and/or shutter to incident light, for example, to distinguish between ambient conditions and the bright light condition occurring during a welding operation and sensitivity also may refer to shutter response time or to the time required for the circuitry associated with the lens to detect a sharp increase in incident light (e.g., due to striking of the welding arc, etc.) and to switch the lens from the clear state to the dark state. Even another characteristic, which may be considered an operational characteristic, is the condition of the battery or other power source for the shutter, such as the amount of power remaining, operational time remaining until the power source becomes ineffective, etc. In the past various of the operational characteristics of such shutters have been adjustable or fixed.

Dynamic operational range or dynamic optical range is the operational range of the lens between the dark state and the clear state, e.g., the difference between the shade numbers of the dark state and the clear state.

The disclosures of the patents identified herein are specifically incorporated in their entirety by reference.

SUMMARY

An aspect of the invention relates to an auto-darkening lens controller, including a relatively fast acting detector responsive to input light to provide signals representing initiation of a welding operation, and a relatively slower acting detector responsive to input light to provide signals representing continuation of a welding operation.

Another aspect relates to a controller, including a pair of detectors operable in parallel and/or concurrently, one of the detectors having a relatively fast acting component to detect initiation of an event and the other of the detector having a relatively slow acting component to detect the event, whereby the detectors are cooperative promptly to detect the event and to maintain the detection.

Another aspect relates to a method of detecting welding, including detecting initiation of welding using a relatively low sensitivity, faster acting detector, and detecting continuation of welding while filtering non-welding events using a relatively higher sensitivity, slower acting detector.

Another aspect relates to a method of enhancing operation of an auto-darkening lens control that has a detector and associated circuitry to detect initiation of welding substantially independently of time based filtering and to maintain detecting of welding using time based discrimination, including coupling control signals and power to an auto-darkening lens via a substantially unimpeded path from a detector to the auto-darkening lens.

Another aspect of the invention relates to a multistage control for an auto-darkening lens (ADL) includes an ADL controller to operate an ADL to respective light transmissive/blocking modes, a first relatively lower sensitivity signal detector responsive to the initiation of welding to operate the ADL controller to cause the ADL to reduce transmission, a second relatively higher sensitivity signal detector responsive to continuation of welding, and a filter associated with said second signal detector to filter non-welding events from causing the second signal detector falsely to detect at least one of cessation of welding and continuation of welding.

Another aspect relates to a method of operating an ADL, including using a relatively lower sensitivity detector responsive to initiation of welding, operating an ADL to reduce transmission of light, using a relatively higher sensitivity detector, detecting continuation of welding to maintain the ADL in reduced transmission mode, and filtering non-welding events (NWEs) from affecting the relatively higher sensitivity detector.

As will be described further below, the present invention is directed to a variable optical transmission controlling device and to associated sensing and control circuitry and functions. The device is described in detail with respect to use in a welding helmet. However, it will be appreciated that the device may be employed in other environments and in other devices and systems for controlling transmission of electromagnetic energy broadly, including, but not limited to optical transmission. As used herein with respect to one example, optical transmission means transmission of light, i.e., electromagnetic energy that is in the visible spectrum and which also may include ultraviolet and infrared ranges. The features, concepts, and principles of the invention also may be used in connection with electromagnetic energy in other spectral ranges.

The present invention is useful for eye protection by an automatic darkening light shutter in a helmet or goggle assembly or in another device, if desired. The switching mechanism for powering the light shutter on and off and/or for selecting operational characteristics may be an integral part of the light shutter and/or frame assembly or other component or portion thereof.

The light shutter of the present invention may be used in a variety of embodiments and applications. The shutter is adjustable to control light, i.e., to increase or to decrease the amount of the incident light which is transmitted through the shutter. When welding is not occurring, for example, the shutter in a welding helmet may be substantially optically clear or transmissive or at least minimizes its attenuation of light. When welding is occurring, the shutter may be dark or closed to reduce the amount of light transmitted therethrough in order to protect the eyes of the person performing the welding and maximize his or her viewing comfort. In both cases, though, the image characteristics of the light preferably remain intact. A photosensitive device may be used to sense the intensity of light impinging in the area of the shutter so as to provide an input to a drive circuit for the shutter in order to control opening and closing thereof.

These and other objects, features, advantages and functions of the invention will become more apparent as the following description proceeds.

It will be appreciated that although the invention is described with respect to one or more embodiments, the scope of the invention is limited only by the claims and equivalents thereof. It also will be appreciated that if the invention is described with respect to several embodiments, features of a given embodiment also may be used with one or more other embodiments.

Also, although the invention is described with respect to a welding shutter (also known as a light shutter) used in a welding helmet for eye protection therein, it will be appreciated that the various features of the invention may be used in conjunction with other devices and functions.

To the accomplishment of the foregoing and related ends, the invention, then, comprises the features hereinafter described in the specification and particularly pointed out in the claims, the following description and the annexed drawings setting forth in detail certain illustrative embodiments of the invention, these being indicative, however, of but several of the various ways in which the principles of the invention may be suitably employed.

BRIEF DESCRIPTION OF THE DRAWINGS

In the annexed drawings:

FIG. 3 is a schematic block diagram of a multi-stage control for the auto-darkening lens;

FIG. 4 is a schematic block diagram illustrating a method in accordance with the invention;

FIG. 5 is a schematic block diagram of another portion of a method in accordance with the invention;

DESCRIPTION

Figure 1:
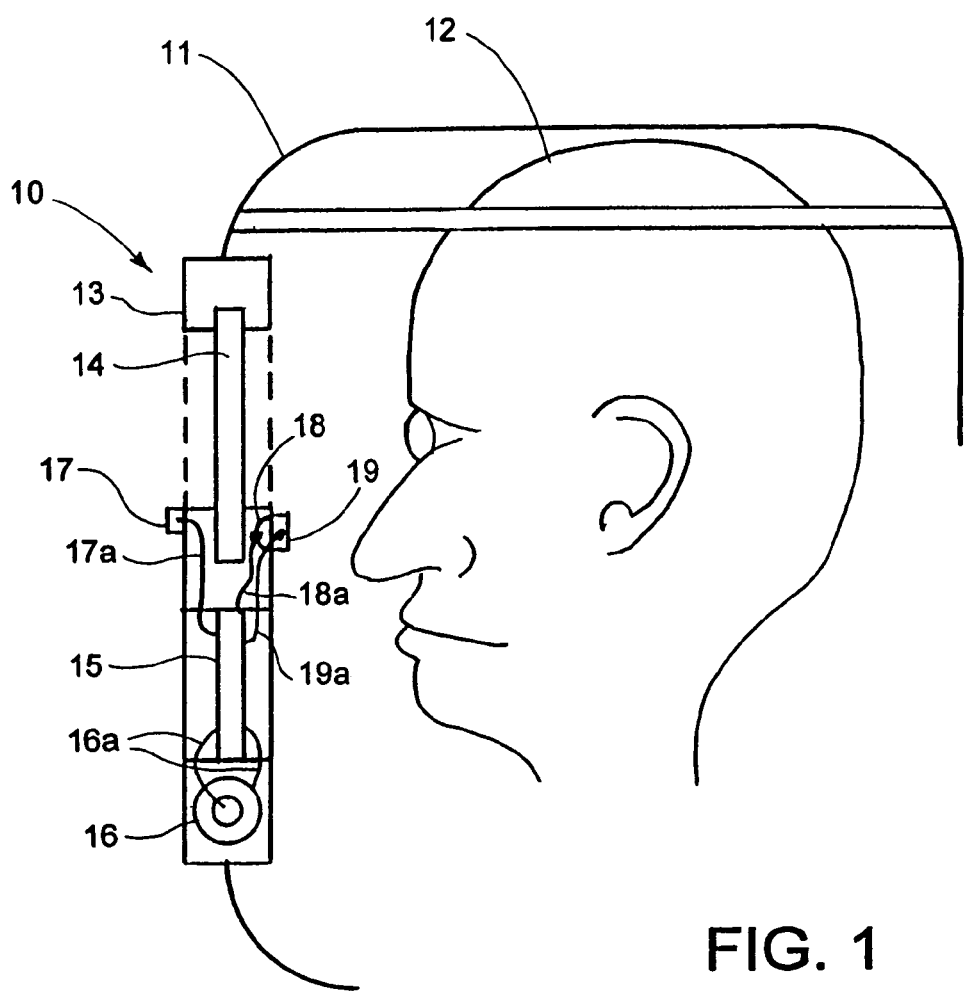
FIG. 1 is a schematic side elevation view, broken away, of an auto-darkening lens in a welding helmet in place on the head of a wearer.
Figure 2:
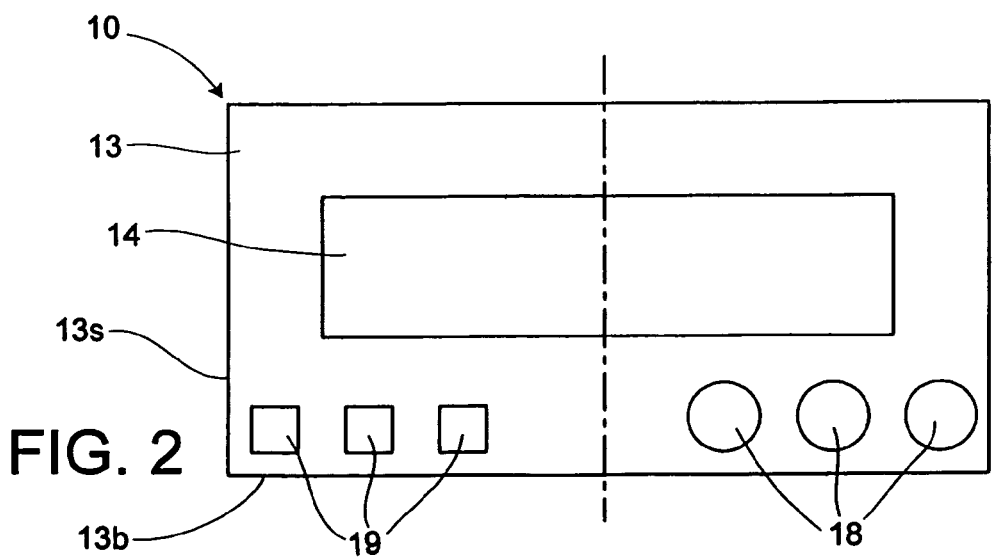
FIG. 2 is a back plan view of the auto-darkening lens of FIG. 1.

Referring, now, to the drawings, and initially to FIGS. 1 and 2, an auto-darkening lens 10 is illustrated in a welding helmet 11 in position on the head of a wearer 12 (sometimes referred to as a user). In the description below primed reference numerals are used to represent parts that are similar to parts that are designated by the same unprimed reference numeral. In the description below reference to directions, such as horizontal, vertical, left, right, up, down, is for relative reference only and is not intended to be limiting.

The auto-darkening lens 10 includes, for example, a support structure or housing 13, a variable light transmission shutter 14 mounted with respect to the support structure, operating circuitry 15 and power supply 16. The shutter may be of a type described in the above patents or another controllable variable light transmission device. Connections 16a couple the power supply 16 to provide power to the operating circuitry 15. Associated with the operating circuitry 15 is a photosensor 17, which is coupled to the operating circuitry by connections 17a, to sense occurrence of or a condition requiring a need for the auto-darkening lens 10 to darken or to lighten, e.g., to decrease light transmission during welding or to increase light transmission in the absence of welding. The operating circuitry 15 operates the auto-darkening lens to various conditions of light transmission. Several control buttons and switches schematically shown at 18 in FIG. 2 are coupled by connections 18a to the operating circuitry 15 and may be operated by the wearer 12 to turn on the operating circuitry 15 to operate the shutter 14,
e.g., to adjust desired shade, to set delay time, to set sensitivity, etc. The operating circuitry 15, power supply 16, photosensor 17, and buttons and switches 18 may be mounted on, in or part on and part in the support structure or may be otherwise located, as may be desired. In use of the auto-darkening lens 10 in the welding helmet 11, a wearer 12 may turn on the power and set the desired dark shade of the shutter 14 by using the buttons and switches 18; and the wearer then puts the welding helmet 11 on the head with the shutter in front of the eyes for viewing work. The shutter 14 may be in its relatively clear or high light transmission condition (or state) to allow the wearer to view the work; and upon sensing occurrence of welding, the photosensor 17 indicates the same to the operating circuitry to cause the shutter to assume a dark or relatively reduced light transmission condition (state). When welding ceases, the operating circuitry allows the shutter to return to the relatively clear condition. Indicators 19 indicate operating conditions of the auto-darkening lens 10. The indicators are coupled at 19a to be controlled by the operating circuitry 15.

Figure 6:
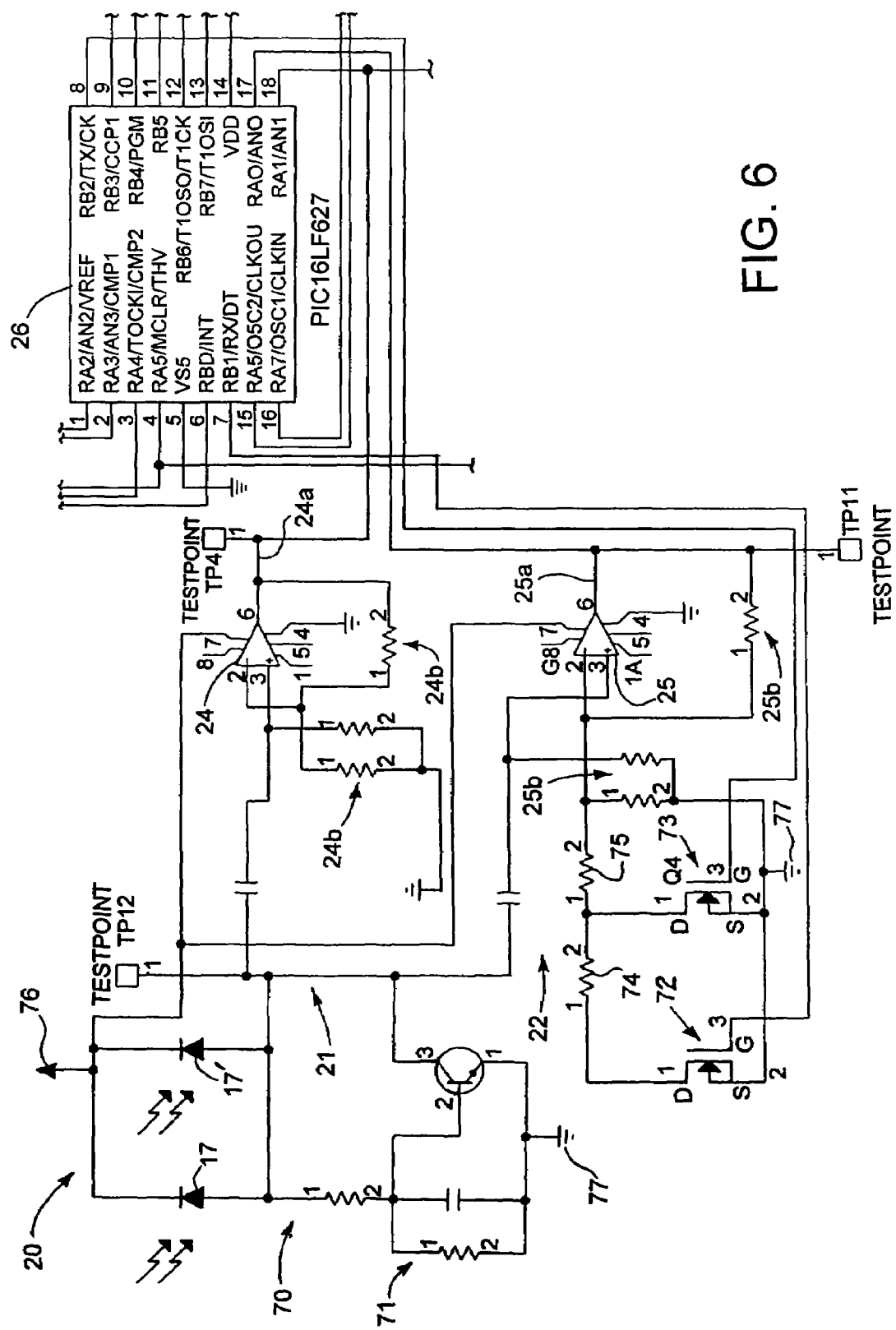
FIG. 6 is a schematic electric circuitry diagram of a portion of a multi-stage control.

Turning to FIG. 3, an example of a multi-stage control 20 illustrating the invention as used for an auto-darkening lens 10 is illustrated schematically. A portion of the multi-stage control 20 also is illustrated in FIG. 6, which is described further below. The multi-stage control 20 may be a portion of the operating circuitry 15, and the multi-stage control as shown is an illustrative example of a circuit embodying features of the present invention. As will be described further, the multi-stage control may be an active discrimination filter, e.g., to discriminate or to filter those frequencies of sensed inputs that can occur at particular levels or frequencies, e.g., the opening of a door to allow in outside ambient light, or repetitive signals, such as occur due to light pulsations so they do not interfere with correct welding detection and operation of the auto-darkening lens 10.

The multi-stage control 20 provides for operating the auto-darkening lens 10 in a manner that allows for time based filtering without having to sacrifice fast switching speed to turn the shutter 14 to dark in response to the initial occurrence of and detecting of welding. As is described further below, in a sense two sensor/detector systems in effect are used to provide a fast sensing and a slow sensing and response to welding.

The multi-stage control 20 includes two signal detectors 21, 22. The signal detectors 21, 22 receive an input from the photosensor 17, which is coupled to both signal detectors. Such input is representative of light incident on the photosensor. If desired, each signal detector may receive an input from a separate photosensor, such as photosensors 17 and 17', the latter being illustrated in dotted outline in FIG. 3 to indicate it is an alternative possibility in accordance with the invention. In the case of two photosensors being used, each may be coupled to a respective signal detector to provide a respective input thereto representative of light incident on the photosensor.

The signal detector 21 is responsive to the initiation of welding to operate the auto-darkening lens 10 to cause it to reduce light transmission. The signal detector 22 is responsive to continuation of welding to maintain the auto-darkening lens 10 in the reduced transmission mode or dark state as welding continues after it has been initiated. In response to an input from the photosensor 17 (or from respective photosensors 17, 17', the invention will be described below with respect to a single photosensor, but it will be appreciated that two or more photosensors or other input devices representative of welding may be used to provide inputs to the signal detectors 21, 22) that would indicate initiation of welding, the first signal detector 21 responds to cause a voltage control 23 to cause the auto-darkening lens 10 to assume a dark state.

Each signal detector 21, 22 includes an amplifier 24, 25 to amplify the input received from the photosensor 17. Both amplifiers 24, 25 are coupled to a processor 26, which may be a microprocessor, a personal computer, or some other device that is able to respond to the inputs received by it to determine whether or not it is appropriate to provide an appropriate input to the voltage control 23 to cause the auto-darkening lens 10 to go to or to remain in a dark state. A memory 27 is coupled to the processor 26 and will be described further below.

The signal detector 21 may be a relatively lower sensitivity signal detector compared to the signal detector 22. The signal detector 21 may have a relatively low gain, e.g., as compared to the gain of the signal detector 22, thereby to avoid responding to background noise. Therefore, the signal detector 21 is useful to detect initiating of welding when relatively bright light occurs. To assure the auto-darkening lens goes to dark state relatively quickly upon initiating of welding, the signal detector 21 may have a relatively fast time constant or response time compared to the time constant or response time of the signal detector 22. Accordingly, the amplifier 24 output in the signal detector 21 is coupled directly to the voltage control 23 to cause operation of the voltage control 23 to operate the auto-darkening lens 10 to dark state. It is noted here that the illustration in FIG. 3 is schematic and, therefore, reference to a direct coupling, such as was just stated, may include one or more intermediate circuits, connections components, etc.

The signal detector 22 may be a relatively higher sensitivity signal detector compared to the signal detector 21 so as to detect continuation of welding even though incident light received by the photosensor 17 during continuation of welding may be of a reduced or diminished intensity compared to the light that is produced at the initiating of welding. The processor 26 in association with the memory 27 in the signal detector 22 includes circuitry, components, software and/or firmware operable to make a determination of whether input thereto from the photosensor 17 and amplifier 25 represents continuation of welding. The processor 26 may be programmable to determine operation as may be desired. For example, the processor may be programmed to check the nature of the signals sensed by the photosensors(s) 17 and, if appropriate, to adjust sensitivity of a signal detector 21 or 22. Other functions also may be programmed in and for the processor 26 for use in carrying out functions of the multi-stage control 20, etc. The time constant or response time of the signal detector 22 may be slower than that of the signal detector 21 for several reasons. One reason, for example, is to allow adequate time for the signal detector 22 to determine whether input information or signals to it represent a continuation of welding. Another exemplary reason is to allow the signal detector 22 to operate the voltage control 23 to maintain the auto-darkening lens 10 in dark state during what may otherwise tend to appear as, but not be, a cessation of welding. For example, due to sputtering that may occur during welding light intensity from the welding may fluctuate. Also, light produced by welding may fluctuate due to fluctuation of the power of an AC power input to the welding apparatus during electric arc welding, etc.

As it is illustrated in FIG. 3, the multi-stage control 20 may use a single photosensor or group of photosensors 17 from which respective taps are coupled to the signal detectors 21, 22. However, as was mentioned above, separate photosensors (or groups of them) may be coupled to the respective signal detectors 21, 22. Since the signal detector 21 is higher speed than the signal detector 22, the signal detector 21 may have faster time constant or faster response photosensor and associated circuitry than the signal detector 22. Since the signal detector 22 may have a relatively slower response, the photosensor associated with it may be that of the type used in a camera. The photosensors detect appropriate light, e.g., visible, ultraviolet (UV), and/or infrared (IR) or some other wavelength(s) as may be desired. Similarly, if the sensor is other than a photosensor, it would be selected appropriately to detect inputs that are to be monitored by the multi-stage control 20.

It is possible that repetitive signals (or other signals of known character) may influence detection of welding by a control for an auto-darkening lens. For example, fluorescent lights, sodium vapor lights, or some other lights may provide a somewhat pulsating light output at 60 Hz (Hertz) or 120 Hz (or at some other frequency). Other ambient conditions in addition to such pulsating light also may affect the accuracy of detection of continuation of welding. Information concerning such ambient conditions and/or repetitive signals (or other signals that can be discerned) may be stored in the memory 27 and used by the processor to reduce or to eliminate the affect of the conditions represented thereby on the effective operation of the signal detector 22. As but one example, a fluorescent light may provide a pulsating light effect that is sensed by the photosensor 17, which provides a representative signal input to the amplifier 25 that amplifies such signal; the processor 26 stores a representation of such amplified signal in memory 27. Thus, the processor 26 is programmable to respond to such stored signals, e.g., to filter them from signals that may otherwise indicate continuation of welding or cessation of welding. The processor and associated circuitry is adaptive in that such signals representing ambient conditions or the like can be updated as may be desired to cause the multi-stage control 20 to adapt to current conditions.

While it is used to detect continuation of welding, the signal detector 22 may use the information from memory 27 to filter the signal received by the processor from the amplifier 25 to remove the affect of the pulsating fluorescent light. For example, the processor 26 may compare the signal it receives from the amplifier 25, which represents light detected by the photosensor 17, with the stored signal in memory 27, filter the stored signal from the signal from the amplifier and then determine whether the output from the processor would be appropriate to operate the voltage control to cause the auto-darkening welding lens to remain in the dark state.

Therefore, if the amplified signal received by the processor 26 fluctuates according to the repetitive fluorescent light frequency, this would not cause a continuation of welding to be indicated or continuation of dark state of the auto-darkening lens 10. However, if the amplified signal received by the processor 26 is random, e.g., as may occur during sputtering in the course of welding, continuation of welding would be detected and indicated and, accordingly, the auto-darkening lens would remain in the dark state.

Briefly referring to the voltage control 23, such element may include appropriate circuitry to provide power to the auto-darkening lens 10. Such element also may include circuitry to respond to appropriate inputs from the amplifier 24 of the signal detector 21 and from the amplifier 25 and processor 26 of the signal detector 22. In response to either or both of such appropriate inputs, e.g., sufficiently large signals, the voltage control provides power to operate the auto-darkening lens to dark state, e.g., drive it to dark by providing suitable electrical input thereto; or, in the instance of welding not being detected, the voltage control allows or causes the auto-darkening lens to assume the clear or bright state.

Turning, now, to FIG. 4, a block diagram 40 or process diagram (sometimes referred to as a flow chart) representing several steps in the process of carrying out the invention, for example, using operating circuitry 15 including a multistage control, such as the multistage control 20, is illustrated. In the block diagram 40, the operating circuitry 15, including the multistage control 20, is on ready to detect welding. At block 41 the operating circuitry 15 and multistage control 20 are initialized and at block 42 they are allowed to stabilize. At block 43 ambient conditions (or information representing the same) are detected, e.g., by the photosensor 17 detecting or sensing various ambient lighting conditions, such as light from fluorescent lamps in the area or environment where welding is to be carried out. At block 44 the ambient information detected at block 43 is stored, for example, in the memory 27; for example, the ambient conditions detected by the photosensor 17 result in a signal provided by the photosensor to the amplifier 25 and from the amplifier to the processor 26 for storage in the memory 27 for subsequent use to carry out the filtering described herein.

Other information also may be stored in memory, such as, for example, information representing the type of welding, whether sputtering is expected to occur, whether signals above or below a certain threshold level should be monitored and considered or should be disregarded, etc. Information also may be provided manually, as at 45, such as manual adjustments to appropriate controls or the like associated with the auto-darkening welding lens, such as the buttons and switches 18 mentioned above.

At block 46 the filter function to be carried out during welding by the processor 26 and memory 27 may be adjusted. For example, in response to detecting a given ambient condition, such as pulsating light from one or more fluorescent lamps, rotating fan blades in front of a light source, outside ambient light conditions, which may change at a relatively slow rate according to cloud movement, etc., signals representing the same that may be stored in the memory at block 44 are used to adjust offsets, and/or to provide information for the processor 26 to carry out filtering functions, e.g., as was described above, during the detecting of the initiating of welding and the continuing of welding and the non-detecting of welding when welding is not occurring. A loop line 47 indicates that the filter function carried out as described or otherwise may be continuously adjusted, e.g., as ambient conditions change.

Referring to FIG. 5, a block diagram 50, process diagram or flow chart representing several steps in the process of carrying out the invention is illustrated using a multistage control, such as, for example, the multistage control 20. The subportion 51 of the block diagram 50 represents operation of the signal detector 21. At block 52 in response to the photosensor 17 sensing light representing initiating of welding, such initiation of welding is detected by the signal detector 21. Initiating of welding usually causes a relatively bright light to occur. Since such light is relatively bright, the signal detector 21 does not usually require as high sensitivity to detect such light as the signal detector 22 requires to carry out its function. However, ordinarily the auto-darkening lens 10 would operate as fast as reasonably possible to achieve dark state upon initiating of welding, and, therefore, the speed of operation, e.g., the time constant, of the signal detector 21 may be relatively faster than the speed of the signal detector 22. At block 53 as a result of such detection of initiating of welding the auto-darkening lens 10 is caused to go to the dark state.

Subportion 54 of the block diagram 50 represents operation of the signal detector 22. At block 55 the output from the photosensor 17 (or 17') and the amplifier 25 is detected or sensed and is applied to the processor 26. At block 56 the processor 26 determines whether initiating of welding has been detected by the signal detector 21, e.g., based on the output from the amplifier 24 from the signal detector 21, which is applied to the processor 26. At block 56 the processor 26 also determines whether if welding had been detected had it been continuing up to the instant point in time when the determination is made at block 56. Thus, at block 56, if the initiating of welding had not been detected, or ceasing of welding had not been detected or determined, then loop line 57 is followed back to block 55 until the answer at block 56 is yes/affirmative. While the loop including line 57 is followed, the signal detector 22 would not cause darkening of the auto-darkening lens 10.

If at block 56 it was determined that the initiating of welding had been detected and that welding had not yet ceased, as detected or determined by the multistage control 20, for example, then an inquiry is made at block 58. At block 58 such inquiry is made whether the signal detected by the photosensor 17 is due to a filtered signal. This function may be carried out as was described above by using the processor 26 to make a comparison with or subtracting a signal that was stored in memory 27 by the processor 26, e.g, a repetitive signal due to light fluctuations of local fluorescent lighting, rotating ceiling fan blades, etc. If the signal detected at block 55 is due to a filtered signal rather than due to welding, then loop line 59 is followed back to block 55 and the just described process of subportion 54 continues repetitively. If desired, while the steps of FIG. 5 are carried out, the filter information at block 46 (FIG. 4) may continue to be updated so the comparison or inquiry made at block 58 is current, e.g., according to current ambient conditions and/or manual setting (see element 45 in FIG. 4).

At block 58 if the signal detected at block 55 is not due to a filtered signal, then line 60 is followed to block 53, and the auto-darkening lens 10 is maintained in the dark state, e.g. by an appropriate signal from the signal detector 22 to the voltage control.

Referring briefly to FIG. 6, a schematic electric circuit diagram 70 is illustrated. The circuit diagram 70 represents a portion of the signal detectors 21, 22 that are responsive, on the one hand, to inputs from photodiodes 17, two of which are illustrated for redundancy. An anti-saturation circuit 71 is coupled to the photodiodes 17. The detector circuits are connected to a processor 26. The processor has a number of input terminals, several of which are shown as unterminated, but which would be coupled to other components in the overall multi-stage control 20. Such unterminated connections may provide respective inputs to the processor 26 and outputs from the processor 26 to carry out the various functions described above, for example.

The processor 26 is coupled to the outputs 24a of the amplifier 24 and 25a of the amplifier 25. The values of the several components, e.g., resistors 24b, 25b that are coupled to the respective amplifiers 24, 25 may be selected to determine the sensitivity/amplification of the respective amplifiers. Several transistor switches or the like designated 72, 73 are coupled to respective resistors 74, 75 and may be operated by the processor 26 to switch those resistors into or out of the circuit associated with the amplifier 25 thereby to change the sensitivity and/or amplification thereof, as may be desired to help assure that continuation of welding will be detected even if the welding light is relatively low intensity. Power to the circuit 70 is provided across terminal 76 and ground 77 from the suitable power source. Operation of the circuit 70 is accordance with the operation described above with respect to the multi-stage control 20.

Figure 7:
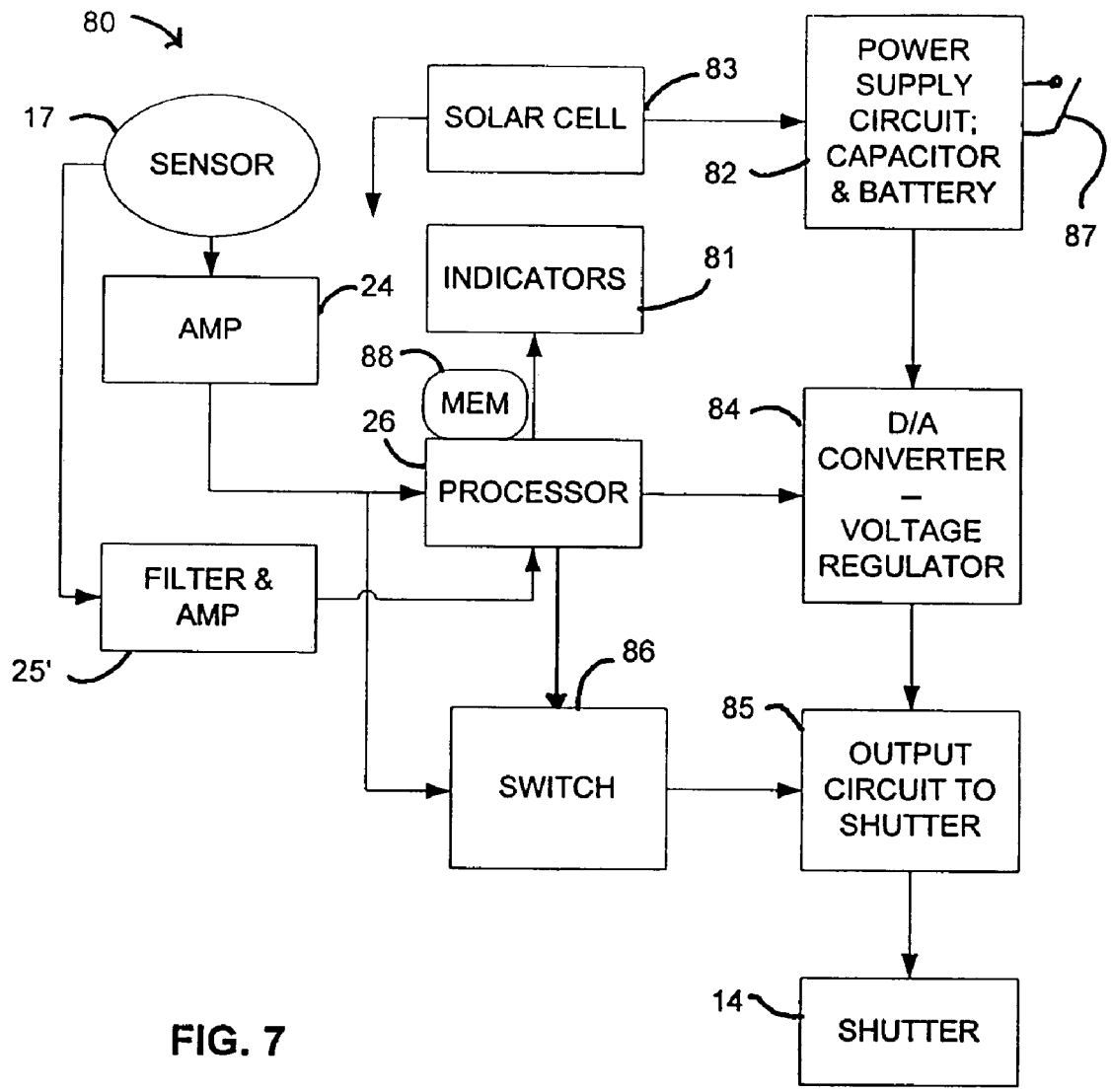
FIG. 7 is a schematic block diagram of a circuit of the invention.

FIG. 7 is a schematic block diagram illustrating an exemplary circuit 80 used in the invention; the circuit 80 may be used as the operating circuitry 15 (FIG. 1). The circuit 80 includes the circuitry of FIG. 6, e.g., the sensor 17, which may be one or more sensors, e.g., photosensitive diodes, the signal detectors 21, 22, and the processor 26. The amplifier 24 of FIG. 6 is shown as amplifier 24 in FIG. 7; the amplifier 25 of FIG. 6 is shown in FIG. 7 as a filter and amplifier 25'. The sensor 17 provides input to the circuits 24, 25'. The amplifier 24 is relatively fast acting and responds quickly to a relatively significant change in brightness of light incident on the sensor 17 that ordinarily would indicate initiation of welding. The filter and amplifier 25' is relatively slower acting than the amplifier 24, and the amplifier and filter 25' functions to remove unwanted frequencies, e.g., 60 Hz. or 120 Hz. of fluorescent lights or some other frequency (ies) so they do not cause a variation in the output of the amplifier and filter 25' that would cause a flickering effect of the shutter 14. The amplifier 24 and the amplifier and filter 25' also may boost the signal representing welding as sensed by the sensor 17 to operate the other parts of the circuit 80, as is described further below. The amplifier 24 also may provide such filtering similar to that provided by the amplifier and filter 25'.

Indicators 81, e.g., light emitting diodes or other indicators, may provide indications of the current state of operation of the circuit 80 and the shutter 14, etc.

A power supply circuit 82, which may include a capacitor and a battery, provides input power to the circuit 80. A solar cell 83 provides input to the power supply circuit 82 to charge the battery and also provides power to other portions of the circuit 80 to reduce the drain on the battery, including when the circuit 80 is on and operating and when it is off, although light still may be impinging on the sensor 17, and when the circuit is in a sleep mode, which is described further below.

Power to drive the shutter 14 to dark is provided from the power supply circuit; capacitor and battery 82. A voltage regulator circuit 84 may be activated to control the voltage supplied to the shutter 14; and an output circuit 85 provides power to the shutter from the regulator 84. A controlling input switch 86, which may be a NAND gate, for example, to the output circuit 85 may be operated to cause power, e.g., voltage, to be supplied to the shutter 14.

When the circuit 80 is off, a capacitor in the power supply circuit 82 may be charged from the solar cell and/or from the battery in or connected to the power supply circuit. In the off state or mode, the various other portions of the circuit 80 may be off, e.g., not operating. However, the solar cell may provide input to the amplifier 24.

The circuit 80 may be turned on by closing an on-off switch 87 at the power supply circuit 82 (or elsewhere In the circuit 80) so that the circuit 80 is ready to detect welding, e.g., by turning on a power connection from the power supply circuit. In response to an input to the sensor 17 that represents welding or at least the initiating of welding operation, the sensor 17 signal promptly is amplified by the amplifier 24 and that amplified signal is directed to the processor 26 to turn it on and to the switch 86 to cause it to operate the output circuit 85 to provide power to the shutter 14. It takes a period of time for the processor 26 to commence its full and proper operation to, among other things, operate the regulator 84. Meanwhile, the capacitor in the power supply 82 and possibly also the battery thereof provide power through the regulator 84 bypassing the regulator function thereof or bypassing the regulator entirely; and that power is provided via the output circuit 85 to the shutter 14.

The welding signal, e.g., light representing continuing of welding, as sensed by the sensor 17 also operates the filter and amplifier 25'. The output from the filter and amplifier 25' is provided to the processor 26 to maintain the processor in operation after it had been awakened by the signal from the amplifier 24. The filter and amplifier 25' also effectively signals the processor 26 to provide an input to the switch 86 causing it to remain in a state of operating the output circuit 85 to provide power to the shutter 14. Since the processor 26 had been awakened, it operates the voltage regulator 84 to regulate the voltage provided to the output circuit 85 and shutter 14. The processor 26 and voltage regulator 84 cooperate to try to maintain a desired level of voltage that is provided the shutter. Such regulation may be by pulse width modulation technique, which is known, and, accordingly, the regulator 84 has a digital to analog converter associated with it to respond to digital signals from the processor to adjust the amplitude of the voltage that is provided to the shutter 14.

The circuit 80 may operate in a sleep mode. In sleep mode the switch 87 may remain closed, but the computer program software (or other program) contained in the memory 88, which is associated with the processor 26, may cause the circuitry 80 substantially to shut down to conserve power if welding had not been detected for a prescribed period of time. The period of time may be, for example, a period during which a user removes the welding helmet 11 and places it on a table during a break time or while the welding helmet is not needed during work. When the circuit 80 is in sleep mode, the capacitor in the power supply circuit 82 may be charged by the solar cell and/or by the battery to assure a suitable stored charge. The circuit can awaken from sleep mode automatically when the sensor senses incident light representing welding or initiation of welding. In such case, the sensor signal quickly is boosted by the amplifier and the boosted signal is directed to commence awakening the processor 26 and promptly to operate the switch 86 to cause power to be delivered from the power supply 82, including the capacitor and/or battery thereof, bypassing regulation (as the regulator 84 takes time to awaken with the processor), to the shutter 14, thus promptly driving the shutter to dark. As the processor 26 continues to awaken and the filter and amplifier 25' provide input to the processor to maintain it in operating mode and providing input to the switch 86 to maintain it in mode to cause the output circuit 85 to provide power to the shutter 14, operation to maintain the shutter dark, as was described above, will continue.

Since the filter and amplifier 25' is relatively slow acting, as the light incident on the sensor 17 varies, e.g., due to relatively gradual fluctuations in ambient light or due to variations in the welding operation, e.g., sputtering, the processor will continue to operate and power will continue to be supplied to the shutter 14 in response to the output from the filter and amplifier circuit 25'.

From the foregoing it will be appreciated that the present invention provides two methods to detect welding, one detects the starting or initiating of welding, and the other detects continuing of welding. The detector 21, including amplifier 24 has relatively lower sensitivity that the detector and amplifier 25 (or filter and amplifier 25'). However, the amplifier 24 and circuitry associated with amplifier 24 are relatively fast acting upon detecting welding promptly to drive the shutter 14 to dark. The amplifier 25 (or filter and amplifier 25'), although slower in response than the amplifier 24, have greater sensitivity so that after welding initially had been detected, the continuation of welding will be detected and indicated although there may be some fluctuations in the light incident on the sensor 17, as was described above. Since it takes time to discriminate between a 60 Hz or 120 Hz light signal from a fluorescent tube and a welding signal, the detector 22, including the amplifier 25 (or filter and amplifier 25'), have adequate time to do the discriminating while the detector 21 and amplifier 24 quickly drive the shutter 14 to dark without having to wait for the time to do the discriminating. Therefore, in a sense the amplifier and filter 25' alone or in collaboration with the processor 26 provide a time based filtering; and the amplifier 24 bypasses that time based filtering so there is no need to wait for the filtering function to be carried out. In an exemplary use of the present invention, the circuit 80 may drive the shutter to dark in hundreds of microseconds, and the shutter then remains dark for a reasonable period of time using charge stored in the capacitor associated with the power supply 82; and by the time the stored charge is dissipated, the processor 26 and associated circuitry, including the amplifier and filter 25' and the voltage regulator have awakened and maintain the shutter dark.

If desired, the closing of the switch 87 may be sensed by the circuit 80 to cause an immediate driving of the shutter 14 to dark, and the shutter would remain dark if welding were detected or the shutter would revert to its relatively clear state if welding were not occurring and being detected.

It will be appreciated that although the invention is described with respect to use of one or more photosensors to sense welding light as a representation of welding, there are other devices used to detect welding, such as current sensors, temperature sensors, and possibly other sensors. Such sensors also may be subject to inputs that are not representative of welding, e.g., a 60 Hz noise signal on an electrical line, etc. It will be appreciated that the invention may be used with such sensors in a manner similar to that described above.

Also, it will be appreciated that although the invention is described above with respect to use in a welding lens system, the invention also may be used with other auto-darkening lenses, such as those that may be used in eyeglasses, safety glasses, sun glasses, goggles, shields used by dentists or other doctors, etc.

A summary of several features of the invention follows: input from the i. Common signal detector and separate signal paths;
ii. Separate detectors;
iii. Photosensor(s)
iii'. Direct path to ADL controller.
iii". Path to filter to help establish start and high level
iv. Photosensor
v. Processor
vi. Programmable
vii. Stabilize according to ambient by sensing non-ambient events
viii. Repeating signals—filter out.
ix. Filter based on time.
x. Filter signals based on changes based on time.
xi. Filter signals based on frequency.
xii. Avoid false triggering.
xiii. Avoid false cessation.
xiv. Active discrimination filter.

xv. 1st or 2nd detectors may have different levels of discrimination.
xvi. Those levels can change or be changed.
xvii. 2nd detector, don't want to set off by other non-welding events.

INDUSTRIAL APPLICATION

It will be appreciated that the present invention may be used to provide detection of an event, e.g., welding, including both the initiation of the event and continuation of the event while filtering undesirable effects from the detecting and/or operation system.

I claim:

1. An auto-darkening lens controller, comprising
a relatively fast acting detector responsive to input light to provide signals representing initiation of a welding operation, and
a relatively slower acting detector responsive to input light to provide signals representing continuation of a welding operation.

2. The controller of claim 1, said relatively fast acting detector having relatively lower sensitivity than the relatively slower acting detector.

3. A controller for an auto-darkening lens, comprising a pair of detectors operable in parallel and/or concurrently, one of the detectors having a relatively fast acting component to detect initiation of an event and the other of the detector having a relatively slow acting component to detect the event, whereby the detectors are cooperative promptly to detect the event and to maintain the detection for controlling the auto-darkening lens.

4. A method of detecting welding, comprising detecting initiation of welding using a relatively low sensitivity, faster acting detector, and detecting continuation of welding while filtering non-welding events using a relatively higher sensitivity, slower acting detector.

5. The method of claim 4, further comprising based on such detecting operating a variable light transmission shutter.

6. A method of enhancing operation of an auto-darkening lens control that has a detector and associated circuitry to detect initiation of welding substantially independently of time based filtering and to maintain detecting of welding using time based discrimination, comprising coupling control signals and power to an auto-darkening lens via a direct path from the detector to the associated circuitry for operating the auto-darkening lens.

7. A method of operating an ADL, comprising
a. Using a relatively lower sensitivity detector responsive to initiation of welding, operating an ADL to reduce transmission of light,
b. Using a relatively higher sensitivity detector, detecting continuation of welding to maintain the ADL in reduced transmission mode, and
c. Filtering non-welding events (NWEs) from affecting the relatively higher sensitivity detector.

8. The method of claim 7, said filtering comprising establishing a profile of such NWEs.

9. The method of claim 8, said filtering comprising at least one of ongoing sampling of NWEs, setting up a NWE profile in memory and rely on that profile to filter the NWEs.

10. The method of claim 7, said filtering comprising ongoing sampling of NWEs.

11. The method of claim 7, said filtering comprising setting up a NWE profile in memory and rely on that profile to filter the NWEs.

12. A multistage control for an auto-darkening lens (ADL), comprising
  a. An ADL controller to operate an ADL to respective light transmissive/blocking modes,
  b. A first relatively lower sensitivity signal detector responsive to the initiation of welding to operate the ADL controller to cause the ADL to reduce transmission,
  c. A second relatively higher sensitivity signal detector responsive to continuation of welding, and
  d. A filter associated with said second signal detector to filter non-welding events from causing the second signal detector falsely to detect at least one of cessation of welding and continuation of welding.

13. The control of claim 12, further comprising a common sensor coupled to the detectors and wherein said detectors comprise separate signal paths for effecting operation of the ADL.

14. The control of claim 12, further comprising a substantially direct path from the relatively low sensitivity signal detector to the ADL.

15. The control of claim 12, wherein the filter filters signals based on changes of time-based signals to at least one of the detectors.

16. The control of claim 12, wherein a sensor provides input to both signal detectors.

17. The control of claim 12, wherein there is a separate sensor for each signal detector.

18. The control of claim 12, further comprising a photosensor to provide an input to at least one of the signal detectors.

19. The control of claim 12, wherein one signal detector has a direct path to the ADL controller.

20. The control of claim 12, wherein a path to the filter helps establish start and high level detection.

21. The control of claim 12, said filter comprising a processor.

22. The control of claim 21, wherein said processor is programmable.

23. The control of claim 22, wherein said processor is an adaptive filter.

24. The control of claim 21, further comprising a memory storing signals for filtering from a signal detector.

25. The control of claim 24, wherein said signals being filtered are other than signals representing welding light signals.

26. The control of claim 12, wherein said filter stabilizes according to ambient by sensing non-ambient events.

27. The control of claim 12, wherein said filter filters repeating signals.

28. The control of claim 12, wherein said filter filters according to at least one of based on time, based on changes based on time, and based on frequency.

29. The control of claim 12, said filter avoiding false triggering of the ADL.

30. The control of claim 12, said filter avoiding detecting false cessation of welding.

31. The control of claim 12, said filter comprising an active discrimination filter.

32. The control of claim 12, at least one of said detectors having multiple sensitivity levels.

33. The control of claim 32, said filter comprising a processor operable to change sensitivity of said at least one of said detectors.

34. The control of claim 12, at least one of said detectors having different levels of discrimination.

35. The control of claim 34, wherein the levels of discrimination is changeable.

36. The control of claim 12, wherein at least one of said detector is set to tend to avoid detecting a signal that is not a welding event.

* * * * *

UNITED STATES PATENT AND TRADEMARK OFFICE
CERTIFICATE OF CORRECTION

| | | |
|---|---|---|
| PATENT NO. | : 7,161,135 B2 | |
| APPLICATION NO. | : 10/884049 | |
| DATED | : January 9, 2007 | |
| INVENTOR(S) | : John D. Fergason | |

It is certified that error appears in the above-identified patent and that said Letters Patent is hereby corrected as shown below:

Assignee (Field 73), replace "Lightswitch Safety" with --LightSwitch Safety--.

Column 2, line 44, replace "disclosed In that" with --disclosed in that--.

Column 11, line 58, replace "elsewhere In the" with --elsewhere in the--.

Signed and Sealed this

Twentieth Day of March, 2007

JON W. DUDAS
*Director of the United States Patent and Trademark Office*